United States Patent [19]

Kalra et al.

[11] Patent Number: 4,912,034
[45] Date of Patent: Mar. 27, 1990

[54] IMMUNOASSAY TEST DEVICE AND METHOD

[75] Inventors: Krishan L. Kalra, Moraga; Katarzyna Pawlak, Oakland; Patricia A. Moon, San Ramon; Larry D. French, Oakland, all of Calif.

[73] Assignee: BioGenex Laboratories, San Ramon, Calif.

[21] Appl. No.: 99,098

[22] Filed: Sep. 21, 1987

[51] Int. Cl.$^4$ .................. G01N 21/78; G01N 33/53; G01N 33/543

[52] U.S. Cl. .......................... 435/7; 422/56; 422/58; 422/101; 422/61; 435/4; 435/805; 436/501; 436/518; 436/524; 436/528; 436/531; 436/548; 436/80708; 436/817; 436/824

[58] Field of Search ............... 436/807, 817, 548, 535, 436/501, 506, 508, 510, 513, 518, 524, 527, 528, 808, 815, 818, 819, 820, 822, 824, 94; 422/56, 61, 57, 58, 101; 435/4, 5, 6, 734, 28, 805

[56] References Cited

U.S. PATENT DOCUMENTS

| | | | |
|---|---|---|---|
| 3,723,064 | 3/1973 | Liotta | 422/57 X |
| 3,888,629 | 6/1975 | Bagslawe | 436/817 X |
| 4,246,339 | 1/1981 | Cole et al. | 435/287 X |
| 4,378,428 | 3/1983 | Farina | 435/7 |
| 4,431,545 | 2/1984 | Pall | 210/641 |
| 4,622,207 | 11/1986 | Wang | 422/56 |
| 4,632,901 | 12/1986 | Valkirs | 436/807 X |

Primary Examiner—Robert J. Hill, Jr.
Attorney, Agent, or Firm—Richard L. Neeley

[57] ABSTRACT

An apparatus is provided for use in an immunoassay for the detection of a target analyte in a liquid sample, comprising a porous reactive filter, having an upper surface and a lower surface, to which is bound an antibody specific for the target antigen; a holder affixed to the porous filter, wherein the upper surface and lower surface of the reactive filter are accessible for passage of liquids through the reactive filter; an absorbent container capable of being detachably attached to the holder; and an absorbent material contained within the container so as to contact the lower surface of the porous filter when the absorbent container is attached to the holder. A prefilter assembly can optionally be attached to the holder so that the prefilter contacts the upper surface of the reactive filter. The prefilter assembly, if present, and the absorbent container can readily be detached from the holder to avoid problems of back flow and to allow ease of storage of the disassembled holder and reactive filter for analysis and comparison with related assays, optionally a series of assays run at different times.

21 Claims, 2 Drawing Sheets

IMMUNOASSAY TEST DEVICE AND METHOD

FIELD OF THE INVENTION

This invention relates to methods and test apparatuses used in immunoassays, particularly involving assays carried out on porous solid substrates to which one member of the antigen/antibody pair is attached.

BACKGROUND OF THE INVENTION

Solid phase reactions for the detection of an analyte in a sample have been significantly improved in the last several decades. In such reactions, the analyte is a member of a specific binding pair, typically either an antibody or an antigen to which the antibody specifically binds, although other binding pair types such as hormone/receptor and sugar/lectin are also used. The non-analyte member of the binding pair is attached to a solid substrate, and a sample suspected of containing the analyte is contacted with the substrate to which the specific binding pair member is attached. If the analyte is present, it is removed from solution by binding to the attached binding pair member. Detection of binding can be accomplished by numerous methods, such as competition for a labeled analyte, reaction of a second binding pair member that is labeled with the bound analyte (e.g., a sandwich immunoassay), or detection of some intrinsic measurable property of the analyte (such as enzyme activity).

In many cases the ease with which specific binding reactions can be carried out has led to the development of assays and test apparatuses designed for home use by an unskilled user or for use by trained non-professionals, such as police officers, under field conditions. When such apparatuses and methods are designed, care must be taken to avoid contamination and other types of improper use so that an accurate and reliable test result is obtained.

One such apparatus is described in U.S. Pat. No. 4,632,901 to Valkirs et al. The apparatus comprises a membrane or filter to which is bound an antibody, typically a monoclonal antibody, over a portion of the surface less than the total surface to which sample will eventually be applied. The apparatus further comprises an absorbent material in contact with the membrane or filter that acts to wick sample through the membrane or filter. Addition of the sample is followed by addition of a labeled antibody directed against the antigen being assayed (i.e., a sandwich assay) followed by a washing step to remove unbound labeled antibody. The absorbent material wicks unbound materials through the filter or membrane and allows reading of results from the upper surface of the membrane or filter to which the original antibody was bound. The reading can be either a visual color change or an instrumental reading, such as by a reflectance spectrophotometer.

U.S. Pat. No. 3,888,629 to Bagshawe describes a reaction cell for the performance of radioimmunoassay determinations and like saturation analysis reactions having supported within it a matrix pad of absorbent material capable of retaining the necessary reagents for the reaction and serving as a site in which the reaction totally occurs. A separable lower chamber is fitted to the lower end of the cell and contains absorbent material to abut the matrix pad and promote filtration through the pad after the reaction has taken place. An upper reservoir chamber fits to the upper end of the cell to contain liquid for passing through the matrix pad. The matrix pad will commonly contain prior to the reaction a predetermined amount of an antigen or antibody in freeze-dried condition.

However, these apparatuses exhibit a number of disadvantages, particularly in terms of the means available for detecting results more than simple positive results (i.e., quantitative or semi-quantitative results are generally not available) and the ability of the user to make a permanent record of the results using the test apparatus, a particularly important application for field testing.

SUMMARY OF THE INVENTION

Accordingly, the present invention provides an apparatus for use in an immunoassay for the detection of a target analyte in a liquid sample comprising a porous reactive filter, having an upper and a lower surface, to which is bound a specific binding pair member capable of binding the analyte; a holder affixed to the porous reactive filter so that the upper and lower surfaces of the filter remain accessible for application and withdrawal of liquids; and an absorbent container capable of being detachably attached to the holder, the absorbent container containing an absorbent material having a surface which contacts the lower surface of the porous filter when the absorbent container is attached to the holder. The apparatus in preferred embodiments further comprises a prefilter assembly capable of being detachably attached to the holder and comprising a porous prefilter affixed to a funneling channel so that when the assembly is attached to the holder and a liquid is added to the funneling channel, the liquid is directed by the channel through the prefilter to the reactive filter.

The related method of the invention is conducted by carrying out an immunoassay, typically in a specifically designed apparatus as described. A liquid sample is contacted with an upper surface of a porous reactive filter, having an upper and a lower surface, to which a specific binding pair member capable of binding the analyte is bound. The reactive filter is affixed to the holder so that the upper and lower surfaces are accessible. The lower surface of the reactive filter is in contact initially with a removable absorbent material, generally contained in a container that is removably attached to the holder. In preferred embodiments, particularly when using urine or blood, a prefilter assembly is attached to the holder so that a prefilter contacts the reactive filter. The prefilter is typically removed after sample is added and before the reactive filter is contacted with some or all of a reagent composition capable of producing a permanetly detectable reaction product to an extent that depends on the amount of analyte present in the sample. Additional steps of the method include separating the container from the holder and storing the holder for later detection of the reaction product. By providing a separable holder with a permanently detectable reaction product on the reactive membrane, analyses carried out at different times can readily be compared to each other.

For certain analyses, advantages are further achieved by binding different amounts of analyte-specific binding pair members to different areas of the reactive filter to provide a readily detectable semiquantitative result either for use in an individual analysis or for comparison in a series of analyses taken at different times.

The apparatus and method of the present invention provide a number of advantages relating to ease of analysis and availability as a permanent storage medium. These and other advantages will be more apparent as the details of the apparatus and method are discussed.

BRIEF DESCRIPTION OF THE DRAWINGS

The invention will be better understood by reference to the following detailed description of specific embodiments when considered in combination with the drawings that form part of this specification, wherein.

DETAILED DESCRIPTION OF SPECIFIC EMBODIMENTS

Figure 1:
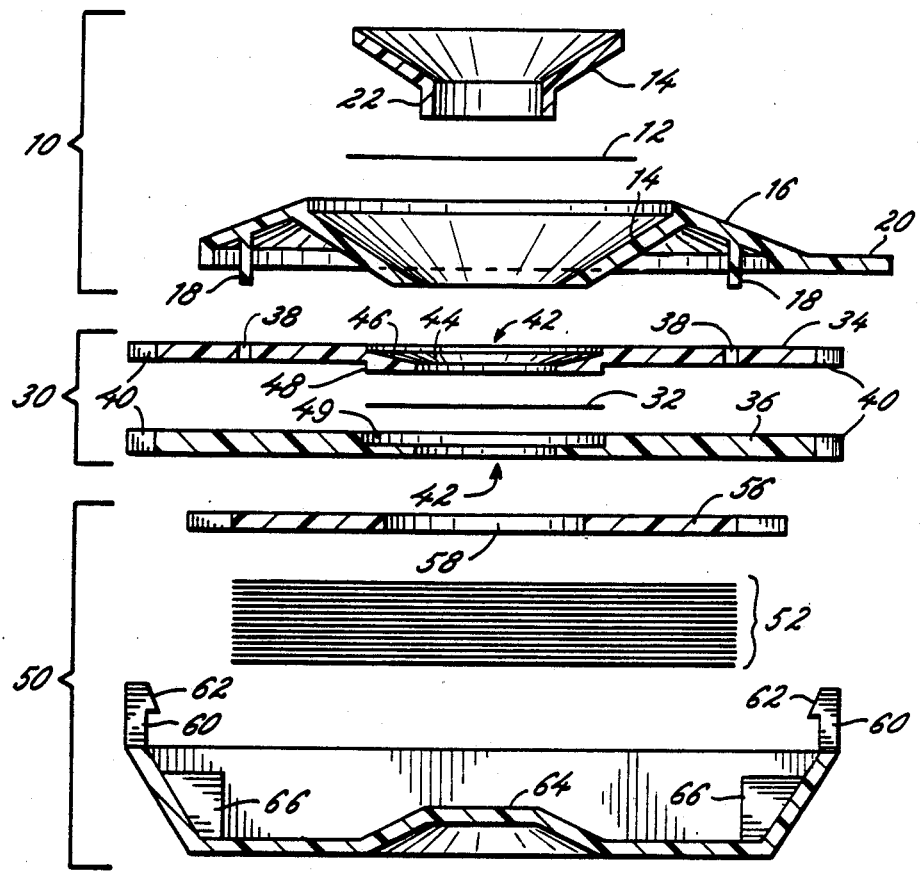
FIG. 1 is an expanded cross-sectional view of an apparatus of the invention showing separately a prefilter unit (10), a reactive filter unit (30), and an absorbent unit (50).
Figure 3:
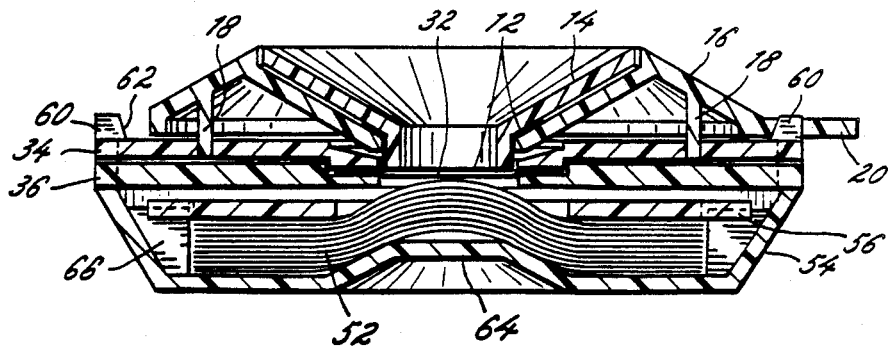
FIG. 3 is a vertical cross-sectional view of the device (when assembled) containing all three of the separable units set forth in FIG. 1.

As shown in the Figures and described herein, the apparatus of the present invention comprises two or in some cases three separate units that can be attached and detached from each other during operation. The two principal pieces are a reactive filter unit 30 and an absorbent unit 50. The reactive filter unit comprises a reactive filter 32 and a holder (in the embodiment shown prepared from two press-fit pieces 34 and 36) to which the reactive filter 32 is affixed so that its upper and lower surfaces are accessible. The absorbent unit comprises a container base (54) and an absorbent material 52 capable of contacting the lower surface of reactive filter 32 when the holder and absorbent container are assembled. A retainer 56 can be present either as an integral part of container base 54 or as a separate piece in order to hold absorbent 52 in place after disassembly of the holder and absorbent container.

The reactive filter 32 is so designated to indicate its function of providing a matrix in which various reactions will take place. The reactive filter can either be a standard depth filter or a porous membrane and is prepared of biologically inert material. Typical reactive filters are thin and microporous and have a multiplicity of interconnected passageways or pores of a size between about 25 nm and 25 μm. The pores and/or passageways can occupy from about 40 to about 80% of the filter volume. Such filters are well known and readily available in commerce. In some cases commercial filters are available that have immobilized to their internal and/or external surfaces a reactant for the attachment of biological molecules, such as antibodies or antigens, to the surfaces. Examples of various filters include cellulosic filters (filter papers), polyamide membranes (e.g., numerous variations of polyamide membranes are manufactured by the Pall Corporation), and various other microporous membranes, such as those available commercially from Amicon, Geleman, and Schleicher & Schuell. For example, the following membranes are available from Pall Corporation: Biodyne ®, a N66 polyamide microporous membrane (U.S. Pat. No. 4,340,479); Carboxydyne ®, a hydrophilic, microporous, skinless nylon 66 membrane with control surface properties characterized by carboxyl functional groups at its surfaces; and Immunodyne ™, a modified Carboxydyne ® membrane prepared by treating a Carboxydyne ® membrane with trichloro-s-triazine. Other microporous membranes, prepared by the Millipore Corporation, are described in U.S. Pat. Nos. 4,066,512 and 4,246,339.

Reactive filter 32 is affixed to the holder by any means capable of retaining the filter in place during the various assembly and disassembly operations of the two (or three) parts of the apparatus as described herein. Suitable means include adhesives, friction (e.g., trapping the membrane between two surfaces that are tightly attached together, such as upper and lower filter holders 34 and 36 of the Figures), and ultrasonic welding. There is no requirement that the holder completely surround the filter, although a preferred embodiment comprises a holder, consisting of one or more pieces, having a channel to which the reactive filter is affixed in a manner that obscures the channel. The term "affixed" is intended to indicate that separation of the affixed items is unlikely to occur during normal operation of the device, including any assembly and disassembly operations. For two items to be affixed to each other, it is not required that they cannot be disassembled, merely that disassembly is unlikely to occur when separating the three units of the apparatus from each other. For example, in the embodiment shown in the Figures, the filter membrane is trapped between two surfaces that are held together by friction fittings, the same type of fittings that attach the prefilter assembly to the holder. However, the degree of friction holding the various parts together can be adjusted so that disassembly of the prefilter assembly from the holder does not disassemble the holder itself.

Means for properly registering the holder to other pieces of the apparatus during assembly are preferably provided. In the Figures, groove 40 is designed to fit cooperatively with projection 60 of absorbent container 50 so that the absorbent is in proper register with and contacts the lower surface of reactive filter 32. Corresponding projections and recesses, male and female threads, and separate bolts with holes in both adjacent units are examples of the many numerous known techniques for providing proper register between parts of an apparatus.

Attaching means must also be present in order to hold the various parts together during operation of the apparatus. These attaching means can be the same as the means for properly registering the various units or can operate independently of the registering means. In the Figures, prefilter assembly base 16 is attached to top portion 34 of holder 30 by means of a projection 18 that fits tightly into recess 38, thereby providing a friction fit. Absorbent container 50 is attached to holder 30 by means of projections 60, each projection having a catch 62 that retains holder 30 when holder 30 is assembled to absorbent container 50 by pressing holder pieces 34 and 36 (already assembled) onto the assembled absorbent container 50 so that projections 62 engage grooves 40. Other types of projections, catches, male and female threads, bolts, temporary adhesives, and the like can be used to attach the various parts together.

Since the present apparatus is designed to be used in a method for detecting a target analyte in a liquid sample, a reagent must be provided for detecting the analyte. As is typical of such assays, the analyte and another molecule form a specific binding pair which interact with each other in a unique way. Examples of such binding pairs include antigens and antibodies, hormones (and other intracellular messengers) and cell receptors, and sugars and lectins. Either member of the specific binding pair can be attached to the filter with the other member being the analyte being detected in the sample. It should be realized that the use of terms such as antigen and antibody are not mutually exclusive since antibodies can act as antigens for other antibodies.

Because of the relative ease with which specific antibodies can now be prepared against antigens, preferred embodiments of the invention use monoclonal or polyclonal antibodies attached to the filter to detect the presence of their specific antigen in a liquid sample. The monoclonal antibodies can belong to any of the classes or subclasses of antibodies, including IgA, IgD, IgE, IgG (subclasses 1-4, if human; 1, 2a, 2b, 3, if murine), or IgM. Actively binding fragments of antibodies can also be employed, such as Fab, Fv, F(ab')$_2$, or the like. The monoclonal antibodies can be prepared by any convenient means which provides immortalization of the B-lymphocyte genes expressing the antibody sub-units, such as fusion between sensitized lymphocytes and a myeloid fusion partner; transformation, e.g., with Epstein-Barr virus (EBV); or other immortalization techniques. Alternatively, the genes can be isolated from a lymphocytic host expressing the antibodies and transferred to a more convenient host for expression in accordance with known genetic engineering techniques.

The antibodies can be obtained from any convenient vertebrate source, such as murine (e.g., rat and mouse), primate (e.g., human), lagomorpha, bovine, ovine, equine, porcine, etc. The antibodies are often prepared by fusing spleen cells from a host sensitized to the antigen with myeloma cells in accordance with known techniques or by transforming the spleen cells with an appropriate transforming vector to immortalize the cells. The cells can be cultured in a selective medium, cloned, and screened to select monoclonal antibodies that bind the designated antigens.

Techniques for attaching specific binding pair members such as antibodies to various solid substrates, such as filters, are well known and need not be described here in detail. Examples include physical absorption or adsorption and chemical binding to a modified or unmodified membrane. See, for example, U.S. Pat. No. 4,376,110 and the references cited therein.

In a preferred embodiment of the invention, semiquantitative analyses can be provided by preparing a reactive filter comprising non-overlapping areas to which different predetermined amounts of the specific binding pair member is attached. This provides areas that have different threshold detection limits. When a reagent combination is used to provide a permanent detectable signal on the different areas, easy comparison between areas or between filters prepared at different times can be made.

The amount of reagent attached to different areas is selected by the user depending on the detection limits one wishes to impose on the technique and the particular reagents being used. Two examples are set forth later in this specification.

Absorbent container 54 can be prepared in any shape or form so as to be adapted to hold absorbent 52 in contact with reactive filter 32. Registration and/or attachment means (shown as projection 60 in the Figures) properly orient the two units and/or hold them together. An optional retainer 56 can be present to hold absorbent 52 in container 50 and can either be part of the container base 54 (for example, by an inward projection extending above the absorbent) or can represent a separate retainer that is either removably attached or permanently affixed to base 54 after absorbent 52 is placed in the base. Absorbent material 52 can be any material capable of wicking liquid through capillary action, such as cotton or paper. Various absorbent materials are described in U.S. Pat. Nos. 4,632,901 and 3,888,629. Examples include cotton and other natural or processed vegetable fibers, wool or other processed or natural animal fibers, cloth, paper, artificial fibers such as microporous glass or plastic, and the like.

An optional part of the apparatus is a prefilter assembly unit 10 comprising prefilter 12 affixed to a funneling channel (14 in the Figures shown). Other components, such as the prefilter base 16 shown in the Figures, can be present to complete the prefilter assembly. In the embodiment shown in the Figures, prefilter 12 is affixed to the prefilter assembly by means of a friction fit between funneling channel 14 and prefilter base 16. Such other means for affixing the prefilter to the prefilter assembly, as described above for the reactive filter, can also be used.

In embodiment shown in the Figures, projections 18 serve as means for ensuring proper register of prefilter 12 and reactive filter 32 by means of their ability to fit cooperatively into indentations 38 in filter unit 30. Other registration and/or attachment means, as described above for filter unit 30 and absorbent container 50, can also be used.

Prefilter 12 can be similar or identical to reactive filter 32 except that the specific binding pair member that reacts with the analyte is not bound to the prefilter. However, other reagents to selectively remove other components of the sample can be present. The prefilter is typically used to remove particulate material from the liquid sample being tested and is not normally used in later steps of the operation when reagents are being added to the reactive filter to provide a permanently detectable reaction product in the presence of analyte that has been trapped on the reactive filter. However, if the reagents pass readily through the prefilter without reacting (e.g., with trapped contaminants or other sample components), the prefilter can be retained until later (e.g., until a colored reaction product on the surface of the reactive filter is being determined or until the reaction filter unit is being stored).

The Figures provided herewith demonstrate a number of preferred aspects of the apparatus. The apparatus shown in the Figures is designed for ease of assembly in that all parts can be assembled and disassembled without disruption, which allows apparatuses rejected during quality control operations to be recycled for later use, if desired. In a preferred embodiment shown in the Figures, each of the three units comprises two plastic pieces and a filter or absorbent. Prefilter assembly unit 10 comprises prefilter 12 that is held in place between funneling channel 14 and prefilter base 16 which cooperatively fit together with a press fit. A portion 22 of funneling channel 14 projects downward so that section 22 and prefilter 12 extend below prefilter base 16 in order that prefilter 12 can readily contact the upper surface of reactive membrane 32. A tab 20 is provided on one side of prefilter base 16 so that tab 20 extends slightly beyond upper holder plate 34 for ease of removal of the prefilter assembly unit from the holder.

Figure 2:
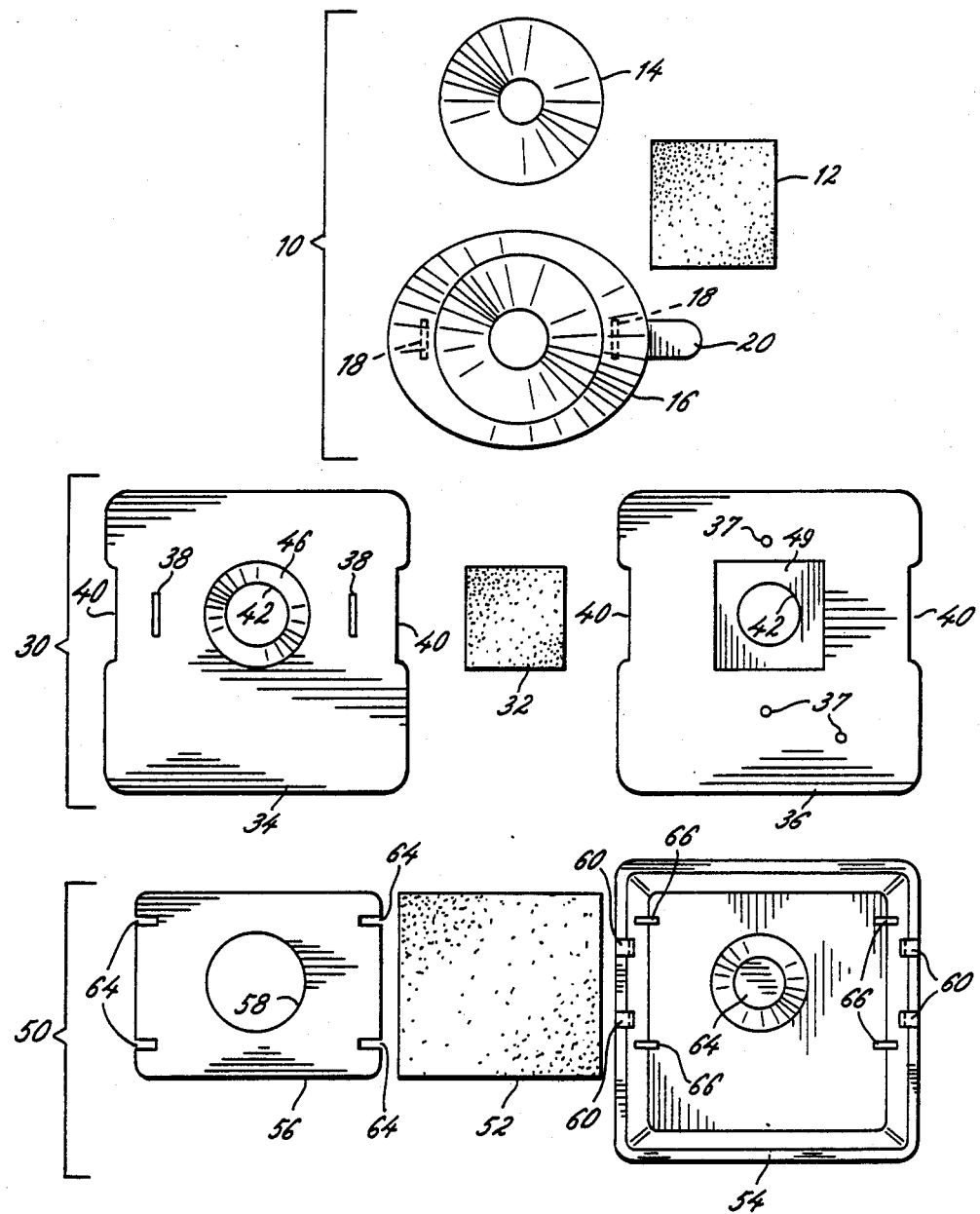
FIG. 2 is a plan view of each of the three units set forth in FIG. 1.

Channel 42 in reactive filter unit 30 is provided with a funneling space 44 with sloping sides 46 so that when the prefilter assembly unit 10 is removed from the reactive filter unit 30, various liquids such as wash or color development liquids can readily be added to the apparatus. A projection 48 is provided on the lower surface of upper holder plate 34 with a corresponding recess 49 in the upper surface of lower plate 36 so that reactive filter 32 can be placed flat between the two holder parts and firmly affixed by assembling the two parts together to form the reactive filter unit 30. The two pieces are held together by projections descending from the lower surface of upper plate 34 (not shown in any Figure because of their location) that fit into recesses 37 in the upper surface of lower plate 36. These projections and recesses are provided asymmetrically as shown in FIG. 2 to prevent incorrect assembly of the apparatus.

The absorbent container is shown with a raised central portion 67 that aids in pressing absorbent 52 against the lower surface of reactive filter 32. Retainer 56 is provided with grooves 67 that fit cooperatively into projections 66 extending upward from container base 54. A channel 58 is present in retainer 56 to allow contact between absorbent 52 and reactive filter 32.

As can be seen in the Figures, a channel for liquids is provided from the prefilter assembly to the absorbent passing through prefilter 12, reactive filter 32 trapped in channel 42 by upper and lower holder pieces 34 and 36, channel 58 of retainer 56, and absorbent 52.

The apparatus of the invention can be used with numerous liquid samples including biological fluids, industrial chemical solutions, waste solutions, and environmental water sources. The method of the invention is carried out by contacting such a liquid sample with the upper surface of the reactive filter. Analyte present in the sample becomes bound to the specific binding pair member that is attached to the filter. Contacting can occur directly or through the prefilter if the prefilter assembly is attached to the holder. Liquid is drawn through the reactive filter by the absorbent in the absorbent container.

The reactive filter is then contacted with the reagent composition capable of producing a permanently detectable reaction product if an analyte is present in the sample and has become bound to the reactive filter. In some preferred embodiments, the reaction product is a visually or spectrophotometrically detectable enzymatic product. Such a product can be formed from an enzyme label that has become attached to the membrane as a result of either the presence or absence of the target analyte. For example, a sandwich assay can be used in which a first antibody is attached to the filter, a specific antigen becomes attached to the first antibody, and a second, enzyme-labeled antibody becomes attached to the antigen. Addition of a substrate for the enzyme results in the production of a product that can be detected. Alternatively, a competitive process can be used in which an enzyme-labeled analyte mimic is added after the sample is added, resulting in a competitive assay. Numerous detection techniques for the presence of analytes bound to a membrane are known and include enzyme color development, fluorescence, retention of colored beads that have become bound together, and radioactive labels. Preferred techniques are development of visible color by enzyme action and use of fluorescent labels.

One requirement of a preferred reaction product is that it be "permanently" detectable. This permanency here does not refer to the continual existence of, for example, a color, since a fluorescent label can be used which is only detectable when irradiated with the proper wavelength of light. However, since the apparatus and method are particularly designed for ease of comparison between results obtained at different times, there should be no significant deterioration in the detectable signal over the time period normally employed for the particular analysis being undertaken. For example, when a test for ovulation by detecting a luteinizing hormone (LH) surge is the assay, stability over at least 10 days is required. Some deterioration in signal strength can occur, but preferably no more than 10%. Detectable labels which meet these criteria include many typically used labels, particularly if stability of only 10 days is required. For permanent reaction products capable of being detected without significant degradation over 3 months or longer, fluorescent labels and azo dyes are preferred. In other cases, as when a legal record of a drug of abuse is being made, permanency may refer to years, in which case azo dyes are particularly preferred. A number of dyes suitable for use with phosphatase enzymes are discussed in two patent applications filed on even date with the present patent application and assigned to the same Assignee, entitled "Stable Indoxyl Phosphatase Substrates" and "Stable Azonaphthol Phosphatase Substrates".

On the other hand, it is not necessary that an apparatus of the invention have a permanently detectable reaction product as defined by the criteria above if it is not intended to be used for comparison of multiple samples or is not intended for long-term storage.

By providing a permanently detectable reaction product and by providing the membrane in a holder that is readily disassembled from the remainder of the apparatus, storage of the membrane and holder for later detection of the reaction product is greatly simplified. Additionally, a translucent membrane can be provided which allows use of a membrane holder adapted to fit in the light path of a transmittance spectrophotometer. Using laser optics, or finely focused beams of light, a quantitative determination of analyte bound to the filter is possible.

If a filter is used comprising non-overlapping areas to which different predetermined amounts of the specific binding pair member are affixed, the different areas can be individually read. Standard apparatuses can be prepared by assembling the reactive filter in the holder and using standard microtechniques to apply small dots of reagent to individual areas of the filter in a set pattern that is repeated from filter to filter. The apparatus described above can readily be adapted to such a use as a result of its ease of assembly and disassembly and its ability to be prepared reproducibly in an asymmetric form, which allows reproducible use of individual apparatuses without reference to standards.

For example, a number of desirable assays cannot be carried out using apparatuses now available which have a single quantity of a binding pair member, such as an antigen, attached to a filter or other solid substrate on which a color is eventually developed by means of a reagent combination. The known apparatuses are useful for detecting a specific level of analyte and giving a yes or no answer and can be adjusted for practically any limit by varying the concentration of reagent bound to the solid phase. However, it is extremely difficult to detect quantitative differences using such a system. In particular, there is generally a limited range of color response after which higher amounts of analyte are undetectable. By providing areas with different amounts of bound antibody, a series of spots or areas is provided, the number of spots being visible depending on the concentration of analyte in the sample.

Examples of assays in which such semiquantitative detection is essential include detection of luteinizing hormone for determining the time of ovulation in women and determining human chorionic gonadotropin (HCG) levels in pregnancy and during various clinical situations. For example, normal levels of luteinizing hormone in women vary from quite low (0–10 mIU/ml) to relatively high (about 30 mIU/ml) when ovulation is not occurring. A surge of luteinizing hormone is indicative of ovulation. However, the surge can range from a small increase of from 30 mIU/ml to 40 mIU/ml (a difference of 10 mIU/ml), a moderate increase of from 5 mIU/ml to 40 mIU/ml (a difference of 35 mIU/ml), or a large increase of from 30 mIU/ml to 200 mIU/ml (a difference of 170 mIU/ml). Accordingly, it is not possible to detect ovulation by merely setting a limit and detecting the presence of luteinizing hormone over that limit. With an apparatus and method of the present invention, the surge can be detected by preparing a series of apparatuses and storing for later comparison. A surge would be indicated by an increase in the number and/or intensity of visible areas after a baseline number had been established.

A similar situation exists for HCG (other than for the initial detection of pregnancy) since levels of 25, 50, or 200 mIU/ml can represent normal values depending on the condition being tested.

The apparatus of the present invention can be provided in a particularly advantageous form by providing a kit comprising multiple apparatuses. Such a kit would also contain the various reagents described herein, such as second antibodies, color development solutions, wash solutions, and the like, for one or more particular assays. Storage space for the disassembled holder can be provided in the kit to allow easy comparison of reactions run at different times.

The invention now being generally described, the same will be better understood by reference to the following detailed examples which are provided for illustration and are not to be considered limiting of the invention unless so specified.

EXAMPLE 1

Assembly of Apparatus for Luteinizing Hormone Test

A two-piece filter holder as shown in the Figures was used along with a 3-micron Pall Immunodyne-activated membrane as the filter. The membrane was cut into 2.0 cm disks and placed between the top and bottom plates (34 and 36) of the holder with the upper (reactive) side showing through the upper plate. The plates were pressed together to provide the assembled holder and filter. In a similar manner, the prefilter assembly shown in the Figures was prepared using a Pall 6-micron glass filter. The filter membrane was cut into an approximately 2.0 cm disk and assembled between the two parts of the prefilter assembly with the smooth side of the filter facing down for eventual contact with the reactive filter. The absorbent container of the Figures was prepared using 15 layers of Viva paper towels as the absorbent. The multiple layers of the Viva towels were placed in the absorbent container. The retainer was placed over the pad of absorbent until the slots in the retainer engaged the tabs in the container, and the assembled container was set aside for later use.

The assembled filter (membrane) and filter holder were then spotted with reagent. Stock solutions of antibody were diluted in phosphate buffer to the appropriate concentration, which was determined by quality control checks of results obtained on assembled apparatuses. The membrane filters were spotted with 30 mIU antigen in phosphate buffered saline using a Hamilton micro syringe. Antibody was then added to a non-overlapping area of the membrane filter. In some instances, a single amount of antibody was added to the membrane filter by syringe. The amount of antibody added was sufficient in some cases to give a color indication equal to the control spot when LH was present in the sample at a concentration of 30 mIU/ml after color development (described later). In other cases, lesser amounts of antibody were spotted on the filter membrane so that the reaction spot matched the control spot at concentrations of either 50 mIU/ml or 200 mIU/ml. These membrane filters having a single concentration of active antibody could be used to determine whether samples were above or below the levels indicated by a color intensity match.

In other cases, several reagent spots were present on non-overlapping areas of a filter membrane with a single (or no) control spot. These membranes were spotted in a circular pattern with the control spot being made at the 12 o'clock position and three antibody spots made at the 3 o'clock, 6 o'clock and 9 o'clock positions to provide 30, 50, and 200 mIU/ml indicating spots as described above for the individual-spot filter membranes. The asymmetric filter holder allowed easy application of spots at predetermined locations that can be readily recognized by the end user.

After the spotting process, the membrane and holder were vacuum desiccated overnight.

The apparatus was assembled from the three individual parts described above by simply pressing the parts together as shown in the Figures. The assembled apparatuses were then placed into heat sealable protective bags and sealed until use.

EXAMPLE 2

Preparation of Reagents

A series of five reagents was prepared for use with the apparatus as described above in the detection of luteinizing hormone:

A. A biotinylated antibody cocktail specific for luteinizing hormone (containing preservatives).
B. A streptavidin-alkaline phosphatase conjugate solution (containing preservatives).
C. A wash solution (containing preservatives).
D. A color development solution containing an enzyme substrate (containing preservatives).
E. A color stop solution to end color development.

A diluent for solutions A and B was prepared containing 0.1N phosphate buffered saline (PBS) buffer, pH 7.6, 0.1% $NaN_3$, 1% bovine serum albumin (BSA), and 0.4% Tween. Prior to use, the solution was filtered through Schleicher and Schuell No. 588 filter paper. Solution A contained anti-LH antibody stock solutions from either Cambridge Biological Supply or other commercial sources that was diluted with diluent to provide the desired protein concentration. The anti-LH antibodies (Cambridge and Terumo) were biotinylated using standard biotinylation techniques. Protein concentration was determined using a standard Bio-Rad protein assay dye reagent. IgG standards were used to prepare a standard curve for spectrophotometric analysis at 280 nm. Standards ranged from 50–700 μg/ml. Samples were diluted to fit the range of calibration, most samples being diluted in the range from about 300–700 μg/ml.

Readings were taken on a standard ELISA Bio-Rad reader with a 600 nm filter and stored in a computer under the "IgG" format. Once initial protein concentrations were determined, they could be adjusted either by diluting with diluent as described above or by concentrating on a Sephadex G-25 column.

Reagent B contained a streptavidin-alkaline phosphatase conjugate prepared from a commercial stock solution (Jackson Immuno Research Laboratories). The commercial freeze-dried powder was reconstituted and diluted to an experimentally determined concentration that gave no background color and the right intensity for control and test spots. For example, lot no. 7579 (product code no. 016-050-084) was diluted with the diluent described above for reagent A in a ratio of 1:87 to give a 10 μg/ml solution.

Reagent C consisted of the diluent described above for use in preparing reagent A.

Reagent D was an indoxyl phosphatase substrate consisting of 250 mg/l 3-indoxyl phosphate, 350 mg/l potassium ferricyanide, 50 mg/l potassium ferrocyanide, 0.1M 2-amino-2-methyl-1,3-propanediol, and 50 mg/l nitrotetrazolium violet (NTV) in a deionized water solution containing 0.05% (w/v) sodium azide and 10 μl/ml DMF (dimethylformamide).

Reagent E was a color-stop solution containing, per 500 ml, 68.5 ml 0.5M citric acid stock solution (citric acid monohydrate in 0.1% sodium azide), 31.5 ml 0.5M sodium citrate stock solution (trisodium citrate dihydrate in 0.1% sodium azide), 125 ml EDTA stock solution (0.2M EDTA disodium salt), 4.0 ml 10% $NaN_3$ stock solution, and sufficient water to provide a total volume of 500 ml. The mixture was prepared in a polycarbonate or glass container and closed until use.

EXAMPLE 3

LH Test Using Apparatus and Method of the Invention

An apparatus of the invention prepared as in Example 1 was used with the reagents set forth in Example 2. The apparatus and reagents were prepared into a kit containing 10 apparatuses assembled with the removable prefilter assembly, 10 urine cups with lids, 10 urine droppers, and 5 bottles containing the reagents indicated in Example 2. The kits were used to determine ovulation in a series of human test subjects. Urine samples were collected between 10:00 A.M. and 8:00 P.M. in the urine cups. In some cases, testing occurred immediately while in other cases the samples were stored either at room temperature for up to 8 hrs or refrigerated for up to 24 hrs.

A urine sample was measured in the provided dropper (0.5 ml). The urine was applied to the apparatus with the prefilter assembly in place and allowed to drain into the absorbent. Four drops of solution A were then added to the test window and allowed to drain through. Four drops of solution B were then added and allowed to drain through. At this point, the prefilter assembly was removed from the apparatus. Five to ten drops of solution C were added to the test window and allowed to drain through. Two drops of solution D were then added and timing was initiated. Thirty seconds after the addition of solution D, 5-10 drops of solution E were added to the test window and allowed to drain through.

After this last step, the holder was detached from the absorbent container and the results determined by visual inspection. Appearance of the control spot (antigen spot) indicated that the antibody and other reagents present in the reagent solutions were working properly.

In most cases this test was carried out using a filter that had been spotted with a single concentration of antibody, as described above in Example 1. The antibody concentration was selected for an individual test subject so that when the second spot appeared in the test window with an intensity equal to or greater than the control spot, a surge in LH level was indicated.

EXAMPLE 4

Semi-Quantitative LH Analysis

An apparatus was prepared as described in Example 1 but not containing a control antigen spot. Instead, four concentrations of an anti-LH antibody were applied to the filter at the 12, 3, 6, and 9 o'clock positions (concentrations of 3, 1.5, 0.75, and 0.375 mg/ml, respectively). The apparatuses were used to determine LH in urine using the procedure set forth in Example 3. Standard test solutions containing 10, 20, 30, 40, 60, 80, and 100 mU/ml of LH were used. Biotinylated anti-LH antibody was used at a concentration of 10 μg/ml with a streptavidin-alkaline phosphatase concentration of 5 μg/ml. Two series of tests were run using different batches of biotinylated antibody. Similar results were obtained in both cases. The 10 mU/ml standard produced a visible spot at the 12 o'clock position and a faintly visible spot at the 3 o'clock position. At a concentration of 20 mU/ml, the first two spots were relatively darker and an extremely faint spot was visible at the the 6 o'clock position. These first three spots continued to darken with a standard 30 mU/ml sample and a faint fourth spot was visible in both cases at the 9 o'clock position. For one of the two biotinylated antibodies tested, a progressive increase in spot color was apparent. Although it was difficult to determine the relative color of the darker spot at the 12 o'clock position, definite differences could be seen in the other spots, particularly the spot at the 6 o'clock position. The colors were stable so that comparisons could readily be made at least one month after the analysis was initially run.

The second series of tests with the second biotinylated antibody also were distinguishable from each other and showed a progressive darkening with increased concentrations of standards. The 100 mU/ml standard produced an apparently anomalous result at the 12 o'clock position where it appeared that not all of the spot reacted, thereby giving a half-moon appearance of the indicator dye at this position. However, this sample could readily be distinguished from the 80 mU/ml standard using the remaining spots at 3, 6, and 9 o'clock so that an observer was readily able to distinguish the 80 from the 100 mU/ml sample.

EXAMPLE 5

Semi-Quantitative LH Analysis

In an experiment similar to that for Example 4, different amounts of an anit-LH antibody were immobilized on the apparatus described in Example 1. Concentrations used were 3.5, 2.3, 1.5, and 1 mg/ml decreasing clockwise from the 12 o'clock position. LH concentrations tested were 20, 30, 35, 40, and 60 mU/ml. A series of biotinylated antibody and strepavidin-alkaline phosphatase concentrations were used to determine the effects of changes in concentration of these reagents on the analysis. Some variation was seen in distinguishing power, indicating that optimal results can be obtained by optimizing the concentration of the components used to develop the color. For example, particularly good results were seen using 1.25 μg/ml of the biotinylated antibody and 5 μg/ml of the streptavidin-alkaline phosphatase reagent. Optimization appears to be readily available by carrying out a series of reactions using different concentrations of filter-bound antibody, second antibody, and enzyme component, as described herein.

EXAMPLE 6

HCG Assay

An assay for human chorionic gonadotropin hormone was carried out using the apparatus of Claim 1 and reagents similar to those used for the LH assay with the following variations. An anti-hCG antibody was prepared in propionate buffer at pH 6 or bicarbonate buffer at pH 9 at a concentration of 4.5 mg/ml. The hCG standard was prepared by diluting a 500 U/ml stock solution in PBS containing 0.1% sodium azide, pH 7.6. The stock solution was diluted to 25 U/ml in the same diluent. The membrane was prepared by spotting 0.5 μl of each sample (antibody and standard) using a Hamilton dispenser and a 25 μl syringe. The absorbent in the absorbent container consisted of Viva paper towels without print, 10 layers of 1×2 inch towels, plus 1.5×1.5 cm Pall Ultipor GF 6-micron filters, glass-side up. The reactive membrane was a Pall Immunodyne 3-micron filter, 1.5×1.5 cm. A Pall UltiporPlus GF U640Z 6-micron glass filter was used as the prefilter, glass-side up. The assembled apparatus was desiccated and stored prior to use.

The HCG test was carried out in a manner similar to that described above for the LH assay. Kits were stored prior to use at 2°-8° C. and allowed to come to room temperature before use. Using a dropper provided with the test kit, 0.5 ml urine (or serum) was added to the top of the prefilter and allowed to flow through. Four drops (120 μl) of the second antibody solution (reagent A, prepared with streptavidin-labeled anti-hCG instead of anti-LH) were then added and allowed to flow through followed by 4 drops of the enzyme complex. At this point, the prefilter was removed and discarded. About 16 drops (0.5 ml) of the wash solution (reagent C) were then added and allowed to flow through. Two drops (60 μl) of the substrate solution (reagent D) were added, and an incubation period of 1 minute was initiated. After the end of the incubation period, about 16 drops (about 0.5 ml) of the stop buffer (reagent E) were added and allowed to soak through. The filter holder was then removed from the absorbent container and results were read.

The control spot reacted with reagents A-E to provide an indication that the test was run properly. Samples containing 50 mIU of analyte (HCG) showed a second spot of intensity at least equal to that of the control spot.

The apparatus shown in the Figures, used for this assay, when disassembled provided a holder that could be stored in a standard 2×2 inch slide holder, allowing samples to be readily stored in a minimum of space without contamination.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An apparatus for use in an immmunoassay for the detection of a target analyte in a liquid sample, comprising:
    a porous reactive filter, having an upper surface and a lower surface, to which is bound a first member of a specific binding pair wherein said specific binding pair comprises said first member and said target analyte;
    a substantially flat holder affixed to said porous filter, wherein said upper surface and said lower surface are accessible for passage of liquids through said reactive filter;
    a prefilter assembly capable of being detachably attached to said holder and comprising a porous prefilter affixed to a funneling channel, wherein said prefilter contacts said reactive filter when said prefilter assembly is attached to said holder;
    an absorbent container capable of being detachably attached to said holder; and
    an absorbent material contained within said container so as to contact said lower surface of said porous filter when said absorbent container is attached to said holder.

2. The apparatus of claim 1, further comprising registering means and attaching means for attaching said holder to said absorbent container in proper register.

3. The apparatus of claim 2, wherein said registration means comprises a projection in a surface of either of said holder or said absorbent container and a cooperating recess or projection in a surface of the other of said absorbent container and holder.

4. The apparatus of claim 1, further comprising registration means and attaching means for attaching said prefilter assembly to said holder in proper register.

5. The apparatus of claim 1, wherein said holder comprises a substantially flat rigid body member having a channel between opposite surfaces of said holder to which said reactive filter is affixed so as to obscure said channel.

6. The apparatus of claim 1, wherein said reactive filter is a microporous membrane or a fibrous depth filter.

7. The apparatus of claim 1, wherein said absorbent container comprises a retaining piece capable of retaining said absorbent material in said container when said container is separated from said holder.

8. The apparatus of claim 1, wherein said reactive filter comprises non-overlapping areas to which different predetermined amounts of said first binding pair member are attached.

9. The apparatus of claim 8, wherein said first binding pair member is specific for luteinizing hormone.

10. A kit for the detection of an analyte, comprising a multiple of apparatuses according to claim 1.

11. The kit of claim 10, wherein said apparatuses are present in a container configured to hold a multiple of holders from said apparatus after said holders are disassembled from said absorbent container.

12. A method of carrying out an immunoassay for detection of a target analyte in a liquid sample and obtaining a permanent record of the assay result, which comprises:
- (1) contacting said liquid sample with an upper surface of a porous reactive filter, having an upper surface and a lower surface, to which a first member of a specific binding pair comprising said first member and said target analyte is attached, said reactive filter being affixed to a substantially flat holder so that said upper and lower surfaces are accessible, the lower surface of said reactive filter being in contact with an absorbent material contained in container removably attached to said holder, whereby liquid in said sample is absorbed into said absorbent material through said reactive filter, wherein said contacting is carried out in the presence of a prefilter assembly comprising a prefilter and liquid channeling means affixed to said prefilter, and wherein said prefilter assembly is detachably attached to said holder so that said prefilter contacts said upper surface of said reactive filter;
- (2) contacting said reactive filter with reagent composition capable of producing a permanently detectable reaction product in an amount determined by the amount of analyte present in said sample;
- (3) separating said container from said holder; and
- (4) storing said holder for later detection of said reaction product.

13. The method of claim 12, wherein said analyte is an antigen and said first binding pair member is a monoclonal antibody specific for said antigen.

14. The method of claim 12, wherein said reaction product is a visible enzyme reaction product.

15. The method of claim 14, wherein said reaction product is an azo dye.

16. The method of claim 12, wherein said prefilter assembly is detached from said holder after Step (1).

17. The method of claim 16, wherein said sample is urine.

18. The method of claim 12, wherein detection of said reaction product comprises absorbance of transmitted light in a transmission spectrophotometer.

19. The method of claim 12, wherein said reactive filter comprises non-overlapping areas to which different predetermined amounts of said first binding pair member are affixed.

20. The method of claim 19, wherein detection of said reaction product comprises determining which of said areas are visible.

21. The method of claim 19 wherein said binding pair member is an antibody specific for luteinizing hormone.

* * * * *